(12) United States Patent
Tedesco Zammarano et al.

(10) Patent No.: US 8,480,639 B2
(45) Date of Patent: Jul. 9, 2013

(54) EYE DROPPER WITH MIRROR

(76) Inventors: Vittorio Tedesco Zammarano, Phoenix, AZ (US); Adam Goldfine, Cave Creek, AZ (US)

(*) Notice: Subject to any disclaimer, the term of this patent is extended or adjusted under 35 U.S.C. 154(b) by 0 days.

(21) Appl. No.: 13/291,403

(22) Filed: Nov. 8, 2011

(65) Prior Publication Data

US 2012/0123357 A1    May 17, 2012

Related U.S. Application Data

(60) Provisional application No. 61/413,017, filed on Nov. 12, 2010.

(51) Int. Cl.
*A61M 35/00* (2006.01)

(52) U.S. Cl.
USPC .......................................... 604/300; 604/294

(58) Field of Classification Search
None
See application file for complete search history.

(56) References Cited

U.S. PATENT DOCUMENTS

| | | | |
|---|---|---|---|
| 2,382,771 A | 8/1945 | Bowers | |
| 2,410,257 A | 10/1946 | Andrzejewski | |
| 3,779,245 A | 12/1973 | Windsor | |
| 3,913,575 A | 10/1975 | Windsor | |
| 4,344,430 A | 8/1982 | Astrove | |
| 2006/0173425 A1* | 8/2006 | Meierhoefer | 604/300 |

FOREIGN PATENT DOCUMENTS

| | | |
|---|---|---|
| DE | 2020706 | 11/1971 |
| EP | 0197344 | 10/1986 |

* cited by examiner

*Primary Examiner* — Leslie Deak
*Assistant Examiner* — Sara Sass
(74) *Attorney, Agent, or Firm* — The von Hellens Law Firm, Ltd.

(57) ABSTRACT

A container containing a fluid for depositing the fluid drop-by-drop into a user's eye, includes a mirror element for reflecting the eye to assist in accurately dispensing the eye drops into the eye. The mirror element may be hingedly attached and rotatable from a closed position to a predetermined open position. Alternatively, the mirror may be detachably attached at a first position adjacent the container and relocatable to a second angularly displaced position to provide a reflection of the eye receiving the eye drops.

17 Claims, 3 Drawing Sheets

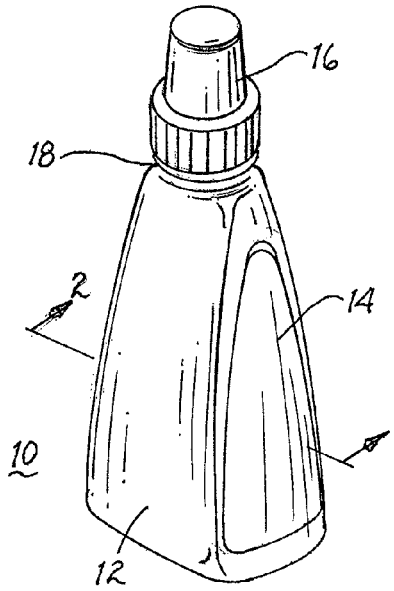
FIG. 1
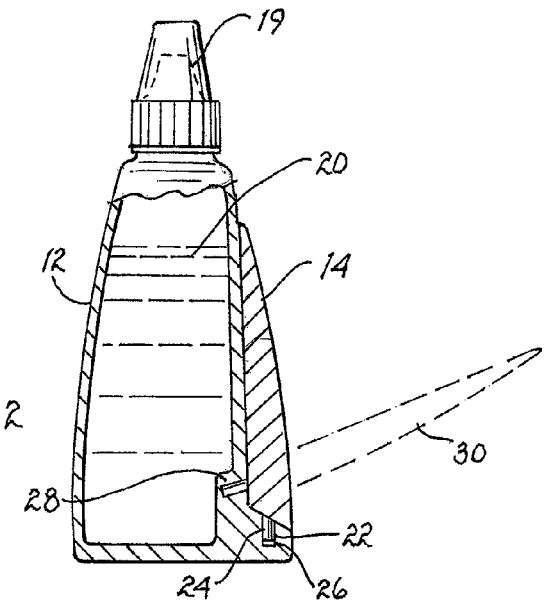
FIG. 2
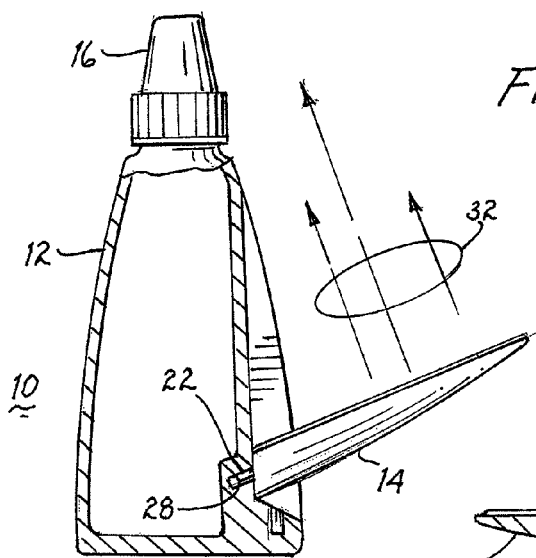
FIG. 3
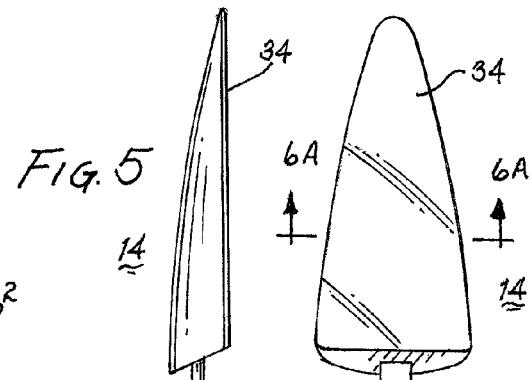
FIG. 4
FIG. 5
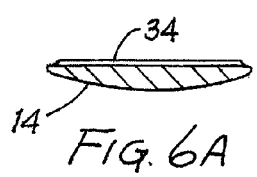
FIG. 6A
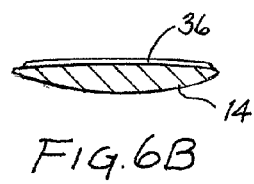
FIG. 6B

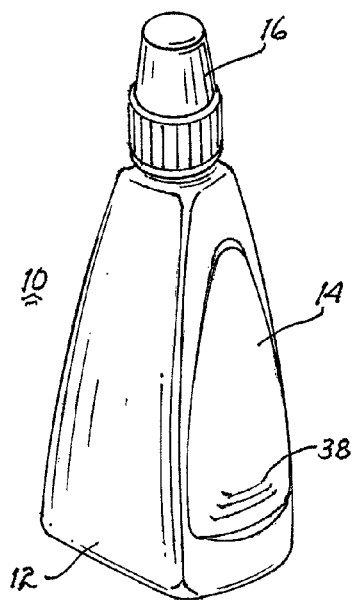
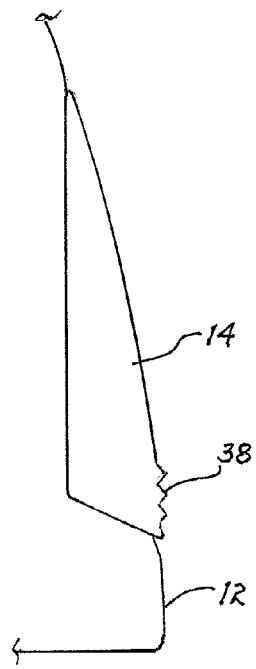
FIG. 7  FIG. 8
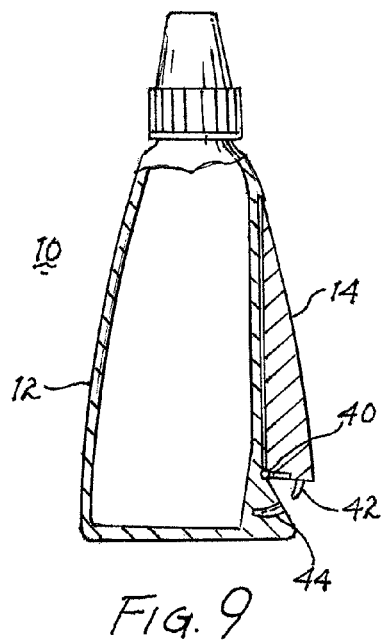
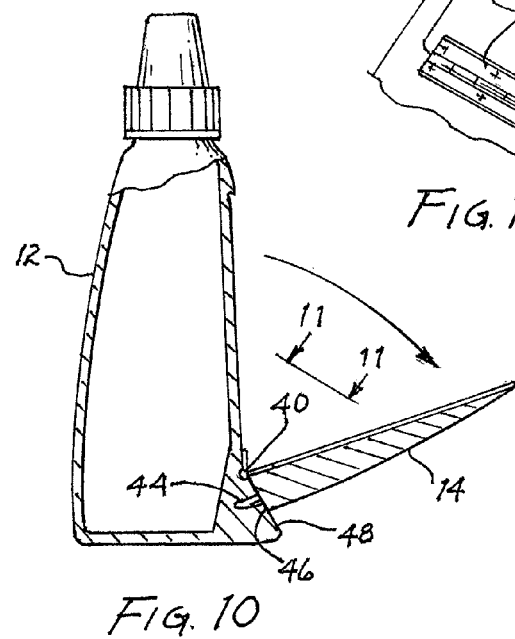
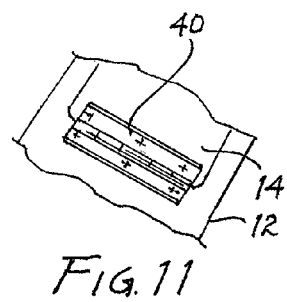
FIG. 9  FIG. 10  FIG. 11

EYE DROPPER WITH MIRROR

CROSS REFERENCE TO RELATED APPLICATION

The present application is related to and claims priority to a provisional application entitled "EYE DROPPER WITH MIRROR" filed Nov. 12, 2010, and assigned Ser. No. 61/413,017, and describing an invention by the present inventor.

BACKGROUND OF THE INVENTION

1. Field of the Invention

The present invention relates to eye droppers and, more particularly, to eye droppers incorporating a mirror to enhance accurate dispensation of eye drops.

2. Description of Related Prior Art

Eye droppers are widely used for purposes of dispensing a lubricating fluid onto the eyeball or for dispensing a liquid medication onto the eyeball. Presently available eye droppers come in many different shapes. Typically, they are cylindrical, oval in cross-section or generally tapered oval in cross-section. Each eye dropper includes a nozzle for dispensing fluid.

Dispensation is generally accomplished by squeezing the eye dropper to expel each drop through the nozzle.

One of the primary problems with presently available eye droppers relates to the general inaccuracy in dispensing a drop or drops onto the eyeball. Usually, a user separates the eyelids with the fingers of one hand and locates the eye dropper above the eyeball with the nozzle pointed toward the eyeball. Depending in part upon the visual acuity at close range of the user, the nozzle may or may not be correctly positioned. When out of position, the drops will fall upon the upper or lower eyelids and serve no useful purpose. To attempt to use a bathroom mirror or the like to assist in accurately positioning the eye dropper is a very difficult task to accomplish because it requires the visualization of the spatial relationships between the reversed image seen in the mirror.

Eye drops sold in relatively small cylindrical containers add a further level of difficulty. These small containers, generally about an inch (2.5 mm) in length and approximately three-fourths of an inch (1.8 mm) in diameter, are not readily flexible. Hence, a degree of force is required to effect dispensation of the eye drops and accurate dispensation of a single drop at a time is difficult to accomplish for many persons, particularly those with limited dexterity in their thumb and forefinger. Moreover, eye drops having medicinal value and generally available only by prescription are sold in such small containers because of the associated costs. When multiple drops are dispensed in error due to the manual dexterity issues, costly waste results.

Various attempts to overcome these problems have been undertaken by using mirrors attached to or attachable to an eye dropper. German Patent No. 2,020,706 discloses a foldable mirror that can be clipped onto a cylindrical body of an eye dropper. By pivoting the mirror to an appropriate angle, the user can see his/her eye to assist in accurately dispensing an eye drop. European patent application No. 0,197,344 discloses a mirror having a receptacle for receiving the bottom of a cylindrical eye dropper to assist in visualizing the eye as eye drops are dispensed. U.S. Pat. No. 2,382,771 illustrates and describes a pivotal mirror attachable to the body of a medicine dropper. U.S. Pat. No. 2,410,257 illustrates and describes a pivotable circular mirror attached to the cylindrical body of an eye dropper having a plunger for dispensing the fluid. U.S. Pat. No. 3,779,245 illustrates and describes a holder for an eye dropper, which holder includes a convex mirror located at the base thereof. U.S. Pat. No. 3,913,575 illustrates and discloses an angularly fixed mirror located at the base of an eye dropper, which mirror is repositionable from being centered upon the axis of the eye dropper to being laterally displaced therefrom for use. U.S. Pat. No. 4,344,430 illustrates and discloses a mirror, arm and an attached clamping arm for supporting an eye dropper to provide a reflection from both eyes of the eye to receive the eye drops.

SUMMARY OF THE INVENTION

The present invention is directed to an eye dropper having a mirror settable at a fixed angle to permit a user to view the dispensing tip of the eye dropper superimposed upon the eyeball of the user to assist in accurately dispensing one or more eye drops. The mirror element in the closed position becomes a part of the eye dropper. In the open position, whether the mirror element is detachably attached or hingedly attached to the eye dropper becomes located at a fixed angular relationship with the longitudinal axis of the eye dropper to avoid any need to adjust the angular orientation of the mirror element.

It is therefore a primary object of the prevent invention to provide an eye dropper with a mirror element contoured to become part of the eye dropper body when in the closed position.

Another object of the present invention is to provide a mirror element hingedly attached to the body of an eye dropper and forming a part of the eye dropper body when in the closed position and at a preset angle when in the open position.

Still another object of the present invention is to provide an eye dropper having a detachably attached mirror element forming a part of the body of the eye dropper when in the closed position and fixedly attached to the body of the eye dropper at a preset angle when in the open position.

Yet another object of the present invention is to provide an eye dropper with an attached mirror element to facilitate accurate dispensation of eye drops into a user's eye.

A further object of the present invention is to provide an eye dropper with a convex mirror element to enlarge a viewed eye during dispensation of eye drops.

A yet further object of the present invention is to provide a compact eye dropper having an associated mirror element.

A still further object of the present invention is to provide a method for facilitating dispensation of eye drops into a user's eye.

These and other objects of the present invention will become apparent to those skilled in the art as the description thereof proceeds.

BRIEF DESCRIPTION OF THE DRAWINGS

The present invention will be described with greater specificity and clarity with reference to the following drawings, in which:

FIG. 1 illustrates an eye dropper incorporating a mirror element;

FIG. 2 is a cross-sectional view taken along lines 2-2, as shown in FIG. 1, and illustrating in dashed lines the mirror element in the open position;

FIG. 3 is a partial cross-sectional view of the eye dropper and illustrating the angle of reflection from the mirror element in the open position;

FIG. 4 illustrates the mirror of the mirror element;

FIG. 5 is a side view of the mirror element;

FIG. 6A is a cross-sectional view taken along lines 6A-6A shown in FIG. 4, and illustrating a flat mirror;

FIG. 6B is a cross-sectional view of the mirror element and illustrating a convex mirror;

FIG. 7 illustrates an eye dropper similar to that shown in FIG. 1 but including ridges disposed on the mirror element to facilitate opening and closing of the mirror element;

FIG. 8 is a partial side view illustrating the ridges shown in FIG. 7;

FIG. 9 is a partial cross-sectional view illustrating a hingedly attached mirror element and shown in the closed position;

FIG. 10 is a partial cross-sectional view similar to FIG. 9 but showing the mirror element in the open position;

FIG. 11 is a partial view of the hinge element taken along lines 11-11, as shown in FIG. 10;

DESCRIPTION OF THE PREFERRED EMBODIMENT

Figure 12:
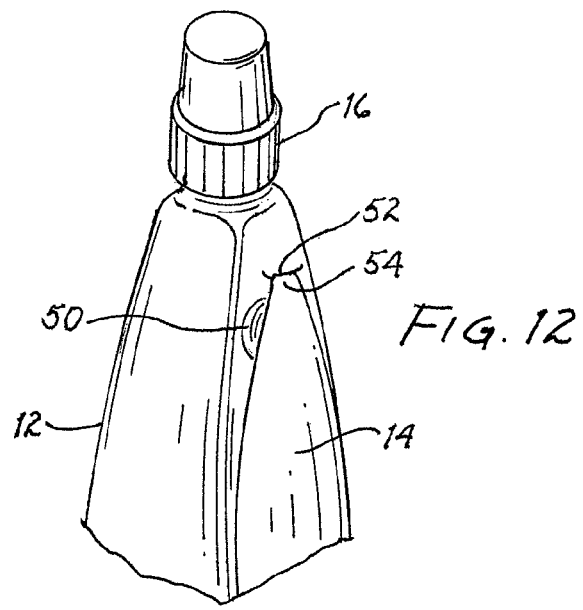
FIG. 12 illustrates a lip for retaining the tip of the mirror element adjacent the container.

Referring to FIG. 1, there is shown an eye dropper 10 formed by a container 12 supporting a mirror element 14. A cap 16 is threadedly engaged with threaded neck 18 to prevent loss of the contents within the container. A nozzle 19 (shown in dashed lines in FIG. 2) extends from neck 18 for dispensing drops of fluid, whether primarily a lubricant or a liquid medicine. As shown, mirror element 14 is located adjacent container 12 and defines an exterior surface which is essentially a continuation of the exterior surface of the container to provide an essentially unitary structure.

As shown in more detail in FIG. 2, a fluid 20 is disposed within container 12 for dispensation through nozzle 19 extending from the container. The mirror element is essentially an extension of container 12, as depicted in both FIGS. 1 and 2. The mirror element includes a peg 22 in engagement with a cavity 24 within base 26 of the container. The engagement of the peg with its cavity, retains mirror element 14 adjacent container 12. To ensure against inadvertent displacement of peg 22 from cavity 24 and possible loss of the mirror element, it is preferable that the peg and the cavity are dimensioned to provide a friction fit. Alternatively, one or both may include roughened surfaces to provide purchase therebetween. To use the mirror element, it is withdrawn upwardly to disengage peg 22 from cavity 24. Thereafter, the peg is inserted into cavity 28. Such reinsertion will locate the mirror element at an angle away from container 12, as depicted by dashed lines 30. To retain the mirror image in its extended position illustrated in FIG. 2, a friction fit between peg 22 and cavity 28 may be employed or the surfaces thereof may be roughened to minimize inadvertent disengagement.

FIG. 3 is similar to FIG. 2 and illustrates peg 22 lodged within cavity 28 to locate mirror element 14 to extend laterally from container 12. Arrows 32 extending from the mirror element depict the line of sight of a user from the mirror element. In essence, this line of sight extends to the eye of the user proximate the nozzle. Thereby, a user will be able to view the nozzle and the eye into which a drop will fall from eye dropper 10.

To prevent rotation of mirror element 14, peg 22 should be other than cylindrical. As shown in FIGS. 4 and 5, the peg may be rectangular in cross-section to prevent rotation of the mirror element about its longitudinal axis. It is to be understood that other configurations of the cross-section of the peg, such as triangular, oval, square, etc., may be used to ensure accurate positioning of the mirror element upon use. Necessarily, cavity 28 is similarly configured.

Mirror 34 of mirror element 14 may be flat, as depicted in FIG. 6A. To enhance visualization of the eye and drops of fluid falling onto the eyeball, mirror 34 may be convex, as represented by numeral 36 in FIG. 6B. However, it is understood that the mirror may be concave.

FIGS. 7 and 8 illustrate a variant of mirror element 14 to facilitate opening and closing of the mirror element. A plurality of ridges 38 may be disposed on the mirror element. This will facilitate upward sliding of the mirror element to disengage the peg from the associated cavity 24. Similarly, it will facilitate reinsertion of the mirror element.

As there is always the potential of inadvertently dropping the mirror element upon disengagement or reengagement of the mirror element with the container, a mechanism for retaining the mirror element attached would be beneficial. Referring jointly to FIGS. 9, 10 and 11, there is shown such a mechanism. A hinge 40 pivotally attaches mirror element 14 with container 12. A peg 42 extends from the bottom of the mirror element for sliding engagement with cavity 44 disposed in container 12. As the movement of the mirror element relative to the container is a pivotal movement, peg 42 must be curved as a function of its radial distance from the pivot axis of hinge 40. Similarly, cavity 44 must be curved to slidingly receive peg 42, as shown in FIG. 10. To provide stability to mirror element 14 upon extending it from container 12, as shown in FIG. 10, it includes a bottom surface 46 that bears against a flat surface 48 of the container. Necessarily, the angle or plane of flat surface 48 must be oriented with respect to the longitudinal axis of the container to correctly position the mirror element to provide a reflection of the eye of a user.

Rather than providing mirror element 14 with a plurality of ridges, as shown in FIGS. 7 and 8, a depression 50 may be formed in container 12 proximate the end of mirror element 14, as shown in FIG. 12. This depression permits a user to use a fingernail to pry the mirror element away from the container. To retain mirror element 14 in the closed position, a lip 52 may be employed in the manner of a snapfit to engage end 54 of the mirror element. It may be noted that FIGS. 13 and 14 show, in cross-section, lip 52 for engaging end 54 of mirror element 14.

Figure 13:
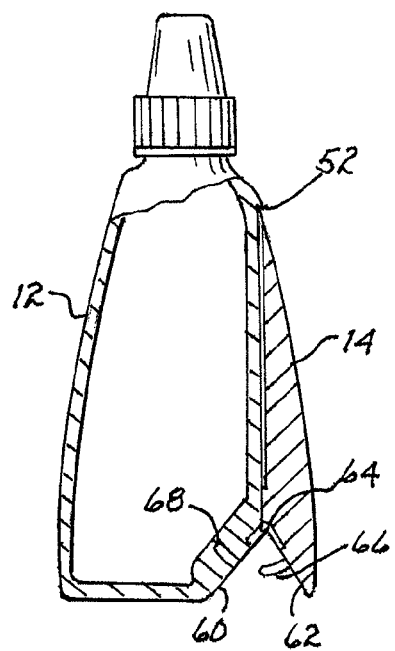
FIG. 13 is a partial cross-sectional view illustrating a variant of the eye dropper shown in FIG. 9.
Figure 14:
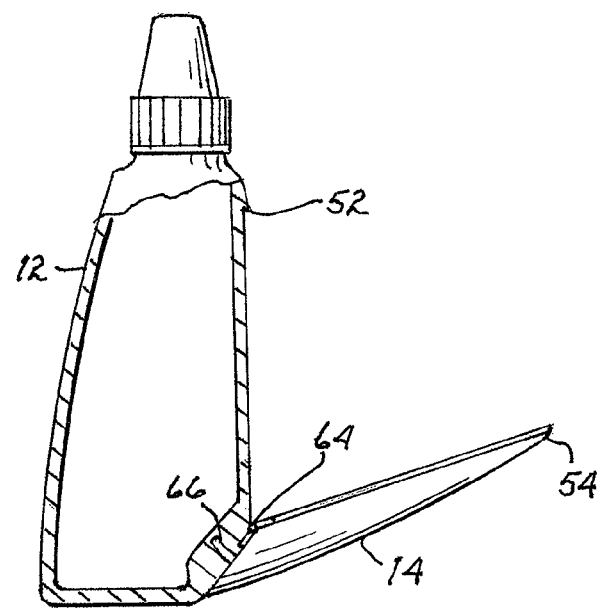
FIG. 14 is a partial view of the variant shown in FIG. 13 with the mirror element in the open position.

FIGS. 13 and 14 illustrate a variant of the hinge and related mechanism shown in FIGS. 9, 10 and 11. Herein, container 12 includes a flat surface 60 extending inwardly from the perimeter of container 12. A hinge 64 attaches mirror element 14 to the container. The mirror element includes a flat surface 62 to mate with flat surface 60 upon opening the mirror element. It is noted that the angle of flat surface 60 relative to the longitudinal axis of container 12 is set to position the mirror image as shown in FIG. 14 and provide to the user a reflection of the user's eye into which fluid is to be dropped. To stabilize mirror element 14 in its open position, a curved peg 66 may be inserted within curved cavity 68 upon opening the mirror element, as illustrated in FIG. 14. As noted above, peg 66 should have a friction fit with cavity 68 to ensure that the mirror element does not become pivotally repositioned when the eye dropper is held upside down above a user's eye. Such friction fit may be established by close tolerances of the peg and the cavity or by roughened surfaces upon either or both the peg and the cavity. As noted above, upon closure of mirror element 14, end 54 becomes engaged with lip 52 to retain the mirror element in its closed position.

We claim:

1. A dispenser for accurately dispensing eye drops into an eye, said dispenser comprising:
   a) a container for housing a liquid to be dispensed into an eye through a nozzle;
   b) a mirror element for reflecting the relative locations of said nozzle and the eye;
   c) apparatus for securing said mirror element directly with said container and for repositioning said mirror element relative to said container from a first position adjacent said container to a second position extending angularly from said container and return; and
   d) said apparatus including a peg extending from said mirror element and a cavity disposed in said container for receiving said peg upon repositioning said mirror element to the second position and a further cavity for selectively reiceiving said peg when said mirror element is in the first position.

2. The dispenser as set forth in claim 1 wherein said peg is a friction fit with said cavity and said further cavity.

3. The dispenser as set forth in claim 1 wherein said peg and said cavity and said futher cavity are other than circular in cross-section.

4. The dispenser as set forth in claim 3 wherein said peg and said cavity and said futher cavity are rectangular in cross-section.

5. the dispenser as set forth in claim 1 wherein said mirror element includes an upwardly tapering mirror.

6. The dispenser as set forth in claim 5 wherein said mirror is convex.

7. The dispenser as set forth in claim 1 wherein said peg, said cavity and said further cavity are curved along their respective longitudinal axis.

8. A dispenser for dispensing eye drops, said dispenser comprising:
   a) a container for housing a fluid to be dispensed;
   b) a mirror element positionable from a first position adjacent said container to a second position extended from said container during dispensation of the eye drops and return;
   c) a hinge formed intermediate said container and said mirror element for pivoting said mirror element from the first position to the second position and return; and
   d) a peg extending from said mirror element for engaging a first cavity in said container when said mirror element is in the second position.

9. The dispenser as set forth in claim 8 wherein said mirror element includes a convex mirror.

10. The dispenser as set forth in claim 8 including a lip formed by said container for detachably retaining said mirror element in the first position.

11. The dispenser as set forth in claim 8 wherein the engagement of said peg with said first cavity is a friction fit.

12. A dispenser for dispensing eye drops, said dispenser comprising:
   a) a container for housing a fluid to be dispensed;
   b) a mirror element positionable from a first position adjacent said container to a second position angularly extended from said container during dispensation of the eye drops and return;
   c) said container including a surface essentially conforming with the surface of said mirror element when said mirror element is in the first position;
   d) a hinge for rotatably attaching said mirror element direcly with said container; and
   e) a peg and cavity combination intermediate said container and said mirror element for engaging said peg with said cavity upon positioning said mirror element in the second position and retaining said peg within said cavity with a friction fit.

13. The dispenser as set forth in claim 12 wherein said mirror element includes a mirror.

14. The dispenser as set forth in claim 13 wherein said mirror is convex.

15. The dispenser as set forth in claim 12 including a lip formed by said container for engaging said mirror element and for retaining said mirror element in the first position.

16. The dispenser as set forth in claim 12 wherein each of said peg and said cavity is longitudinally curved.

17. The dispenser as set forth in claim 12 wherein said surface of said mirror element is planar locatable adjacent said surface of said container, which planar, when said mirror element is in the first position.

* * * * *